United States Patent [19]

Mellors et al.

[11] Patent Number: 4,906,571

[45] Date of Patent: Mar. 6, 1990

[54] CELL SURFACE MODIFICATION USING A NOVEL GLYCOPROTEINASE OF PASTEURELLA HAEMOLYTICA

[75] Inventors: Alan Mellors, Guelph, Canada; Alphonsus E. Udoh, Calabar, Nigeria

[73] Assignee: University of Guelph, Guelph, Canada

[21] Appl. No.: 915,532

[22] Filed: Oct. 6, 1986

[51] Int. Cl.$^4$ ............................ C12N 9/52; C12R 1/01
[52] U.S. Cl. ..................................... 435/220; 435/822
[58] Field of Search ............... 435/200, 201, 183, 262, 435/220, 221, 822

[56] References Cited

U.S. PATENT DOCUMENTS 4,390,629  6/1983  Goldberg et al. ................... 435/220

OTHER PUBLICATIONS

Otulakowsky, G. L. et al, *Infect. Immun.*, 42:64–70, (1983) "Proteolysis of Sialoglycoprotein by Pasteurella haemolytica Cytoxic Culture Supernatant".

*Primary Examiner*—Elizabeth C. Weimar
*Assistant Examiner*—Patricia A. Carson
*Attorney, Agent, or Firm*—Irell & Manella

[57] ABSTRACT

A glycoproteinase derived from the culture of *Pasteurella haemolytica* cleaves carbohydrate antigen markers from glycoproteins forming an integral part of plant and mammal cell membrane without general enzyme digestion of other cell protein. The glycoproteinase is separated from the media containing nutrients which induce *Pasteurella haemolytica* to produce the glycoproteinase released into the media.

6 Claims, 2 Drawing Sheets

CELL SURFACE MODIFICATION USING A NOVEL GLYCOPROTEINASE OF PASTEURELLA HAEMOLYTICA

FIELD OF THE INVENTION

This invention relates to a glycoproteinase for cleaving glycoproteins associated with plant and mammalian cell membranes.

BACKGROUND OF THE INVENTION

Several types of bacterium have the capability of producing enzymes for cleaving proteins, the enzyme being commonly referred to as a proteinase. For most living microorganisms including bacteria, proteinases are an essential part of the metabolic apparatus. Hence many types of proteases have been isolated from cultures of known bacteria. The proteases isolated from a variety of bacterium can be classified according to the pH at which they express optimum activity and the essential amino acid at the active site in the protein digested by the enzyme. They can also be classified on the basis of any specific inhibition or co-factor requirement. Proteases can, therefore, be designated as acid, alkaline, or DFP-sensitive, neutral or metal chelator-sensitive and as thio-proteases. Such proteases may or may not be specific to the digestion and cleavage of specific proteins.

It is also known that a non-protease, neuraminidase is widely distributed in a variety of organisms, such as myxoviruses bacteria and animals. Recently, neuraminidase activity was detected in the culture fluid of *Pasteurella haemolytica,* Otulakowsky, G. L. et al, *Infect. Immun.,* 42, 64–70 (1983). Neuraminidase from these various sources including *Pasteurella haemolytica* hydrolizes terminal sialic acids from glycoprotein and ganglioside oligosaccharides. Neuraminidase in cleaving such carbohydrates from glycoproteins does not in any way cleave the protein at any amino acid sites. However, Otulakowsky et al (supra) discovered that the supernatant from the culture of *Pasteurella haemolytica* not only had neuraminidase activity, but also had proteolytic enzyme activity in releasing sialo glycopeptides from glycoprotein. It was uncertain as to whether or not the enzyme activity was due to a new enzyme or previously known enzymes.

SUMMARY OF THE INVENTION

According to an aspect of the invention, a glycoproteinase for cleaving a protein portion having carbohydrate antigen markers from glycoproteins which form an integral part of plant and animal cell membrane without general enzyme digestion of other cell protein is derived from a culture media of *Pasteurella haemolytica.*

According to another aspect of the invention, a method for producing a glycoproteinase specific for cleaving a protein portion having carbohydrate antigen markers from glycoproteins of plant and mammal cell membranes comprises culturing *Pasteurella haemolytica* in a media containing nutrients which induce *Pasteurella haemolytica* to produce the glycoproteinase and release it into the media.

According to another aspect of the invention, an enzymatic process for modifying mammalian and plant cell surfaces to remove a protein portion having carbohydrate antigen markers from glycoproteins of the cells comprises hydrolyzing the cells with the glycoproteinase prepared by the method, according to this invention, under conditions which cleave from the cell wall glycoprotein the protein portion having the carbohydrate antigen markers. Viable cells are produced with modified cell surfaces and remaining cell protein being generally undigested by the glycoproteinase.

BRIEF DESCRIPTION OF THE DRAWINGS

Preferred embodiments of the invention are shown in the drawings wherein.

DETAILED DESCRIPTION OF THE PREFERRED EMBODIMENTS

Figure 1:
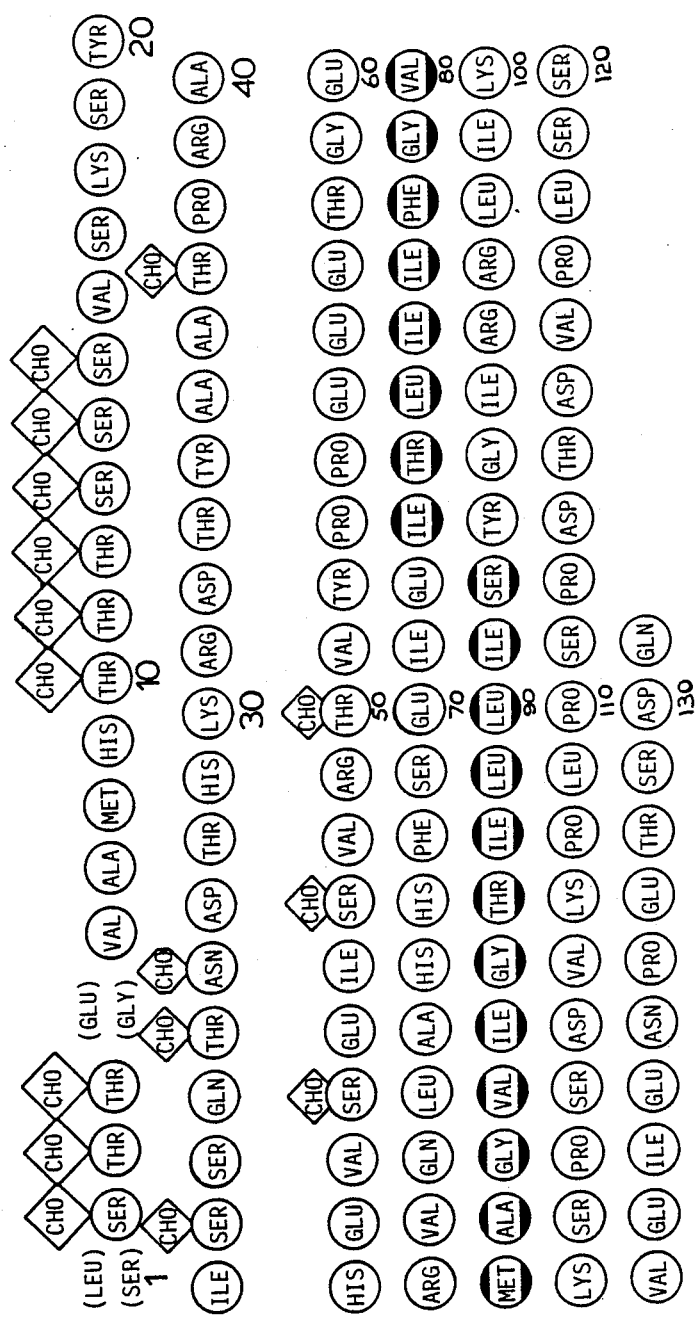
FIG. 1 illustrates the amino acid sequence of a glycoprotein of the erythrocyte membrane.

The glycoproteinase released into the culture medium by *Pasteurella haemolytica* is unique in having the ability to cleave specifically glycoproteins to remove the carbohydrate antigen markers. The protease does not cleave any of the unglycosylated proteins or peptides which may have similar sequences of amino acids to that of glycoproteins. It is, therefore, postulated that the carbohydrate chains on the glycoprotein play an important role during the hydrolysis of glycoprotein with the protease obtained from the culture of *Pasteurella haemolytica.* The protease is capable of cleaving glycoproteins in situ in cell membranes as well as denatured glycoproteins isolated from cell membranes. It has been found that, when the glycoprotein, glycophorin A, is cleaved in situ, there are two major polypeptide products of 24,000 $M_r$ and 12,600 $M_r$, whereas the isolated denatured glycoprotein is cleaved by the protease to yield only the 24,000 $M_r$ polypeptide.

There are twelve recognized serotypes of *P. haemolytica* which are conveniently numbered 1 through 12. Glycoproteinase production has been confirmed in serotypes 1, 2, 3, 5 through 8 and 12. It would appear that little if any glycoprotease is produced by serotypes 4, 10 and 11.

Optimum activity for the glycoproteinase is obtained in the pH range of 7 to 8.5. Prolonged stability of the protease in solution can be maintained at a neutral pH in the range of 7 to 7.6 Storage of the protease at a pH of 8 or above results in irreversible denaturation of the enzyme. The enzyme activity is totally inhibited at pH 4, but the inhibition is reversed by adjusting the pH back to approximately 7 or above without in any way creating or denaturing the enzyme.

The glycoprotease is inhibited by metal chelators and amines at relatively high concentration, such as in the range of 5 to 10 mM. The inhibitors include EDTA, ascorbate, the dicarboxylic amino acids, aspartate and glutamate, inorganic phosphate and to some extent O-phenanthroline.

The glycoprotease is not inhibited by other well known enzyme inhibitors such as PCMB (p-chloromercuribenzoate), PHMB (p-hydroxymercuribenzoate), soya bean, trypsin inhibitor, pepstatin, TPCK (tosylphenylalanylchloromethylketone), and TLCK (tosyllysylchloromethylketone). From these results the glycoprotease is neither a thiol- nor a serine-dependent protease. Inhibition of the glycoprotease by metal chelators indicates that the protease is metal dependent. Even though the enzyme has good activity at pH 8.5, it undergoes irreversible denaturation during storage at pH 8.5. Functional stability of the glycoprotease is maintained only around neutral pH where the enzyme is active so that the enzyme may be classed as a neutral metallo-protease.

The glycoprotease includes an unusual specificity in cleaving glycoproteins. It has been found that the glycoprotease cleaves glycoproteins on the carboxyl side of histidine. From the amino acid sequence of the glycoprotein shown in FIG. 1, considering that one of the major products as cleaved has molecular weight of 24,000, this could only be derived from cleavage of the glycoprotein at the histidine position of 66 or 67. The protease has excellent activity in cleaving sialoglycoproteins which suggests that the carbohydrate components on the amino acid chain are required for enzyme activity. Attempts have been made to add various carbohydrates to the mixture which is being hydrolyzed by the protease and does not in any way affect enzyme activity. The carbohydrate chains responsible for maintaining the sialoglycoprotein substrate in a particular conformation appears to be required by the enzyme. The protease has higher activity with glycoproteins which have a high carbohydrate chain content. For example, the glycoprotease does not cleave fetuin which is a glycoprotein having a very low carbohydrate content ranging from 19 to 24%, whereas the glycoprotease has a very high activity with glycophorin A which has a carbohydrate content of more than 60%. Thus, the glycoprotease is more suited to highly glycosylated proteins.

The glycoprotease activity is associated with a large molecular weight complex which is isolated from the culture of *Pasteurella haemolytica*. The complex is made up of at least five polypeptide chains, one or more of which is the glycoprotease. The polypeptides in the complex are tightly associated. It has been established that the polypeptides are not covalently bound, but are held together by highly stable non-covalent interactions. In addition to the glycoprotease activity of the complex, neuraminidase activity is also found in the complex. By precipitation and isolation of the complex from the culture of *Pasteurella haemolytica*, the enzymes have been purified to specific activities about seventy fold higher than that of the crude enzyme in the culture media, where both enzymes are associated with the complex. The complex is readily soluble in water so that the glycoprotease, even in its unisolated form in the complex, is readily usable in water solutions of concentrations of 70 mg of the complex per ml of water. The lyophilized enzyme complex can be stored at room temperature for at least two months without significant loss in activity, so that the glycoprotease, even in the complex form, is readily usable for cleaving the protein portion having the carbohydrate antigen markers from glycoproteins.

The following Examples demonstrate preferred embodiments of the invention which it is understood do not in way limit the scope of the accompanying claims.

EXAMPLE 1

Preparation of Crude Enzyme

Crude enzyme was prepared as bacterial culture supernatant essentially according to the procedure used by Shewen and Wilkie, Infect. Immun. 35, 91–94 (1982) for the crude toxin preparation, except that the culture time was prolonged.

Lyophilized *Pasteurella haemolytica* serotype 1 culture was reconstituted in RPMI 1640. This was inoculated onto a blood agar plate and incubated at 30° C. for 16–18 h (overnight). Six to eight smooth colonies were picked and inoculated into brain-heart-infusion broth (BHIB) which had been previously equilibrated a room temperature, in 500 ml Erlenmeyer flasks. For large scale preparations, 4–6 flasks were inoculated. The culture was incubated at 30° C. for 4.5 h on a rotary shaker. The culture was then aseptically transferred to sterile centrifuge bottles (250 ml Nalgene screw-capped bottles) and centrifuged at 6,000 RPM (4000 g) for 10 min at 4° C. The pellet from every 200 ml of culture was reconstituted in 3.0 ml of RPMI 1640. The resuspended pellets were pooled and 10 ml inoculated into RPMI containing the desired concentration of heat-inactivated fetal serum (0–7%) This was incubated at 37° C. for 3h with gentle shaking on a rotational shaker. The culture was then centrifuged (at 10,000 RPM,) in sterile bottles and the supernatant was carefully removed and filtered through a 0.45 $\mu M$ Millipore filter. The filtrate was then dialysed against distilled water. The ratio of the volume of filtrate to be dialysed to the volume of distilled water was maintained at 1:6, and three changes of distilled water were made during the dialysis period of 48 h. The dialysed culture filtrate was either lyophilized, or acidified to pH 4.0 with acetate buffer to precipitate the enzyme when this was applicable. Unless otherwise stated, the enzyme preparations used in this study were obtained from serotype 1 culture.

EXAMPLE 2

Partial Purification of the Enzyme by acid precipitation at pH 4

Acid precipitation was used to partially purify crude enzyme which ad either been lyophilized and reconstituted, or was in dialysed culture filtrate.

To any volume of dialysed culture supernatant, sufficient 1.0 M acetate buffer pH 4.0 was added to bring the final concentration of acetate to 0.006 M. A high buffer concentration was used to avoid large volume increases which would make recovery of the precipitates difficult and inefficient. To partially purify samples which had already been lyophilized, the crude enzyme was reconstituted in water as a 20–30 mg/ml solution. Two volumes of 0.01 M acetate buffer pH 4.0 were then added. After the addition of acetate buffer, the samples were left at 4° C. for 30 min. and then centrifuged at 10,000 RPM (47,000 g) at 4° C. for 10 min. The supernatant was easily decanted without any loss of precipitate. The tubes were then inverted over filter paper (usually in a beaker standing on ice) to drain dry. The precipitate was reconstituted by adding 1.0 ml of 0.05 M HEPES buffer pH 8.4 for every 40 mg of crude enzyme treated. The reconstituted acid precipitate was either dialysed and lyophilized or stored frozen without dialysis.

Other useful observations have been made in connection with the use of acid to precipitate the enzyme. One of these is the fact that increased acetate (pH 4) concentration adversely affected the enzyme. For example, when the precipitation was performed in 0.034 M acetate buffer, pH 4.0, instead of the 0.007 M in the recommended protocol, the resultant precipitate was difficult to reconstitute. The reconstituted precipitate gave a much lower specific activity than usually obtained and the purification factor was only 2.2. In addition, the total activity accounted for only about 67% of the activity predicted by the crude enzyme assay.

EXAMPLE 3

Preparation of Red Blood Cell Membranes

Human erythrocyte ghost cells were prepared according to the method of Dodge et al, *Arch. Biochem. Biophys.*, 100 119–124 (1962). Outdated citrated blood 4–6 weeks post-collection, and usually received as 200 ml partially packed units, was pooled and centrifuged in 250 ml bottles at 3,000 RPM (900 g) for 10 min to remove any plasma present. Centrifugation was done at 4° C. using a centrifuge rotor with swing-out buckets. The supernatant plasma, usually heavily colored with haemoglobin from lysed cells, was removed and discarded. The cells were washed with 0.9% (w/v) NaCl (saline) by adding 75 ml of saline to every 25 ml of packed cells, mixing and centrifuging at 3,000 RPM (900 g) for 10 min. Each batch of cells was washed three times. The volume of packed cells obtained after the wash ranged from 60 ml to 110 ml per bag of blood, and was dependent on the post-collection age of the blood. The older units had more fragile cells that underwent massive haemolysis during the wash and consequently yielded a smaller final volume of packed cells.

Cells were lysed by adding 175 ml of 20 mM phosphate buffer pH 7.4 to 25 ml of packed cells in a 250 ml centrifuge bottle. This was mixed and left for 30 minutes at 4° C. before centrifuging at 11,000 RPM (19,000 g) for 40 min at 4° C. The pink supernatant was carefully removed and discarded, and another 175 ml of phosphate buffer added to the residue. After mixing, this was centrifuged again at 1,000 RPM and the supernatant removed again. Six wash steps were usually required to obtain haemoglobin-free ghost cells.

EXAMPLE 4

Preparation of Tritium-Sialylglycoprotein of Erythrocyte Membranes

Sialoglycoproteins of the erythrocyte ghosts were labelled in situ in the membrane by a method based on that of Blumenfeld et al, *Biochem. Biophys. Res. Commun.* 48, 242–251 (1972). A two step procedure is involved in the labelling; the oxidation of terminal sialyl residues with periodate and the reduction of oxidized residues with tritiated sodium borohydride. Initially, the periodate was used in a 2:1 molar ratio to sialic acid residues. The molar concentration of sialic acid in membrane material was calculated by assuming that glycophorin constitutes 10% of total membrane protein (Marchesi, V. T. in G. Weissmann and R. Claiborne (eds) *Cell Membranes: Biochemistry, Cell Biology and Pathology*, pp 45–53, PH publishing Co. Inc., New York (1975)) and that 75% of these are membrane sialoglycoproteins (Marchesi, V. T. et al, *Ann. Rev. Biochem.* 45, 667–698 (1976)) and that 10,000 g of membrane sialoglycoprotein contain 12.1 mol of sialic acid (Winzler, R. J. in A Gottschalk (ed), Glycoproteins, Part B., pp 1268–1293, Elsevier/North Holland Publishing Co., Amsterdam, 1972)). This calculation, however, excludes membrane sialic acid on glycolipids. Occasionally, ghost cells that clumped and would not form a smooth suspension were obtained following labelling. In addition to the molar relationship, the actual concentration of periodate and protein (and therefore of sialic acid) in the medium is important. In later preparations, 2.3 mM final concentration of periodate was used for erythrocyte membrane preparations containing 3.5 mg protein/ml and this ratio gave consistent results. This represented periodate/sialic acid ratios of 1:1.6 and 1:2.6

To label erythrocyte membranes with tritium, the protein concentration of the membrane preparation was adjusted to 3.0–5.0 mg/ml in 0.02 M phosphate pH 7.4 and the ghost cell suspension was warmed to room temperature if cold. Sufficient sodium periodate was then added to bring the final concentration of periodate to 0.5 mg/ml. This mixture was stirred gently at room temperature for 10 min. Two volumes of cold 0.02 M phosphate pH 7.4 were then added and the mixture centrifuged at 11,000 RPM, (19,000 g) for 40 min at 4° C. 180 ml of phosphate buffer was added to resuspend the pellet and this was centrifuged again at 11,000 RPM. After this wash, the pellet was taken up in a minimum volume of buffer to give a final volume of about 1/5 of the initial volume of ghost cells during oxidation with periodate. This suspension was allowed to warm up to room temperature.

To 25 mCi of $NaB^3H_2$, 1.0 ml of 0.002 M NaOH was added. This part of the experiment was performed in the fumehood in a designated radio isotope laboratory. 0.2 ml of the $NaB^3H_4$ solution was added to the suspension of oxidized ghost cells for every 500 mg of protein in the suspension. This was stirred for 30 minutes and at least 5 volumes of cold 0.02 M phosphate buffer pH 7.4 then added. The cell suspension was centrifuged at 11,000 RPM (19,000 g) for 40 min. The pellet was washed at least six times with buffer until the counts in the supernatant became relatively constant. Counts in the supernatants were monitored by withdrawing 0.5 ml of the supernatant after every wash for liquid scintillation counting. Washing was considered complete when the counts (cpm) in 0.5 ml of the supernatant went down to 4,000 or less. At the end of the wash, as much buffer as possible was removed and the pellet stored at −70° C. An aliquot of the pellet was assayed for protein content and radioactivity.

EXAMPLE 5

Preparation of Glycophorin

Glycophorin was prepared from either tritium-labelled or unlabelled cells. The procedure of Marchesi and Andrews, *Science* 174, 1247–1248 (1971) was employed. Freeze-dried labelled or unlabelled ghost cells were suspended in 0.3 M lithium diiodosalicylic acid (LIS) in 0.05 M tris(hydroxymethyl)aminomethane (Tris) hydrochloride pH 7.5 at a concentration of about 25 mg membrane protein/ml. This was stirred at room temperature for 15 min. Two volumes of cold distilled water were added and the turbid suspension was stirred at 4° C. for a further 10 min. After centrifuging at 16,000 RPM ( 20,000 g) at 4° C. for 120 min, the supernatant was removed and preserved and the residue discarded. The supernatant was mixed with an equal volume of freshly prepared 50% phenol in distilled water. The mixture was stirred at 4° C. for 15 min and then centrifuged at 6,000 RPM (4,000 g) for 1 h at 4° C. in a swinging bucket rotor. The centrifuged material separated into two phases: the upper or aqueous phase contained the glycophorin. This was removed and dialysed against four changes of distilled water (50 ml of extract/liter of distilled water) over a 48 h dialysis period. The dialysed material was lyophilized and the dry material was suspended in 100% ethanol at a concentration of 1 mg material/2ml of ethanol and stirred for 2 h at 4° C. This treatment removed LIS and phenol. The sample was then centrifuged at 10,000 RPM (12,000 g) for 20 min to collect the precipitate. The ethanol washing procedure was repeated four times. Since both phenol and LIS gave a positive Lowry reaction, the progress of LIS and phenol removal was monitored by adding 1.0 ml of Lowry reagent A and 0.5 ml of Lowry reagent B to 0.5 ml of the ethanol supernatant obtained after each wash, and watching for the development of a blue color. Color development after the third wash was slow but could usually be observed if the test was allowed to stand for 1 h. Removal of LIS and phenol was regarded as complete when the ethanol supernatant no longer produced a blue color with Lowry reagents after 1 h. At this stage, bound LIS is still present but cannot be removed from the glycophorin.

After the final wash, the residue was suspended in distilled water and dialysed against distilled water for 24 h with two changes of water (ratio of sample to water maintained as above) during the period. The dialysed material was centrifuged at 9,000 RPM ($-10,000$ g) for 30 min at 4° C. The supernatant was lyophilized and the residue was characterized by SDS-PAGE as glycophorin, and its radioactivity determined.

EXAMPLE 6

Protein Determination

Protein assays were usually performed according to the method of Lowry et al as modified by Peterson, G. L. *Anal. Biochem.* 83, 346-356 (1977). Aliquots of the sample to be assayed, containing a maximum of 50 μg protein, were pipetted into appropriate volumes of distilled water in centrifuge tubes to give final volumes of 1.0 ml. 1.0 ml of 0.15% sodium deoxycholate (DOC) was added and the contents mixed. After 10 min at room temperature, 110 ml of 72% trichloroacetic acid (TCA) was added and the mixture centrifuged at the top speed of a clinical centrifuge for 15 min. The supernatant and the tube were inverted over filter paper and allowed to drain for 5 min. 1.0 ml of distilled water was then added to the precipitate. This precipitation step was omitted for protein samples made up in water or phosphate buffer. All samples containing either tris(hydroxymethyl)aminomethane (Tris) or hydroxyethylpiperazineaminoethane sulfonate (HEPES) were taken through the precipitation step because the buffer salts interfere with protein assay by contributing to color development.

The reconstituted precipitate or untreated protein sample in 1.0 ml of distilled water was assayed for protein as follows: 1.0 ml of Lowry reagent A (Peterson, G. L. supra) was added and the sample was mixed and allowed to stand for 10 min. Reagent A was prepared by slowly adding an equal volume of 20% sodium carbonate, while stirring, to a solution of 0.2% copper sulphate ($CuSO_4 \cdot 5H_2O$) containing 0.4% potassium tartrate and then mixing 1 volume of the resultant solution with 1 volume of 0.8 M NaOH, 1 volume of 10% sodium dodecyl sulphate (SDS) and 1 volume of distilled water. Ten minutes after adding reagent A to the sample, 0.5 ml of reagent B (0.33 N solution of Folin-Ciocalteau phenol reagent obtained as a 2 N solution from Fisher Scientific Ltd., Toronto, Ontario) was added and the contents of the tube mixed. The mixture was left at room temperature for 1.5 h before the adsorbance was read at 750 nm using a Beckman DB-GT (grating) spectrophotometer. Tests were usually run in replicate. Protein values were calculated using Peterson's two-point method (Peterson, G. L. supra), in which two protein standards - a high standard h (40 ug) and a low standard l (20 μg) were used to calculate protein values for the absorbance of the unknown.

Thus, $$\text{Protein } (\mu g) = (I \times A_{750})^S$$

where $S = \log(h/l)/\log(A_{750}^h/A_{750}^l)$ and $I=$ antilog $[(\log h)/S - \log A_{750}^h]$. $A_{750}^h$ and $A_{750}^l$ are the absorbances of the high standard (h) and the low standard (l) respectively at 750 nm.

To facilitate initial assessment of approximate protein content of the samples to be analyzed, a standard curve was made by plotting absorbances at 280 nm against unknown concentrations of bovine serum albumin (BSA). Protein solutions to be analyzed, or appropriate dilutions of them, were quickly read at this wavelength using silica cells and the approximate protein content read off the standard curve. All absorbances on the graph above 1.5 were obtained by diluting the appropriate samples 1/10 and then multiplying the absorbances obtained by 10. Suitable aliquots of the protein solutions were then analyzed by the Lowry assay.

β-Mercaptoethanol and diiodosalicylic acid were found to interfere severely with the Lowry method by producing very intense colors. Consequently, the method was adapted for monitoring the removal of LIS and phenol by ethanol from LIS-extracted glycophorin as described above.

EXAMPLE 7

Assay for Enzyme Activity

The following procedure was employed when determining enzyme activity in *P. haemolytica* enzyme preparation or fractions.

Aliquots of the enzyme solution (this varied in volume and protein content) were pipetted into microfuge tubes (usually in duplicates) and 0.1 ml of dilute $^3$H-labelled erythrocyte membrane suspension (0.2 mg protein) in 0.05 M HEPES, pH 7.4 (containing 0.025 M NaCl in most cases) were added. The final volume of each test mixture was 0.2 ml. If less than 0.1 ml of enzyme solution was used, the difference was made up with an appropriate volume of 0.5 M HEPES, pH 7.4. Negative controls containing heat-denatured enzyme were always included. The incubation periods varied between 30 min and 2 h. After incubation, 50 μl of 25% TCA were added to each test and the mixture centrifuged at 13,000 g to pellet the precipitate. One hundred μl of the TCA supernatant was analyzed for radioactivity. The net release of radioactive products by the enzyme was found after subtracting appropriate heat-denatured enzyme control values. The enzyme activity was expressed as radioactivity (cpm) released from tritiated ghost cells. Specific activities were calculated using the protein content of the enzyme solution assayed. The purification factor was calculated as the ratio of the specific activity of the purified enzyme to that of the crude enzyme.

The results in Table 1 (Sections [a] and [b], show the distribution of enzyme activity in the acid fractions. The crude enzyme assay in Section [a] of Table 1 was performed on the undialysed culture filtrate. The total protein content of the culture filtrate used for acid precipitation of enzyme protein was 241.5 ml and the total enzyme activity was $1.79 \times 10^6$ cpm/h. Protein assay separately performed on the acid precipitate (reconstituted) and acid supernatant yielded the respective values of 43.6 mg and 195.2 mg, indicating recovering of 238.8 mg or 99% of initial total protein.

All the enzyme activity was recovered in the acid precipitate, which, in the initial assay, showed a 17-fold increase in specific activity over that of the crude enzyme. No enzyme activity was detected in the supernatant even after this had been dialysed and lyophilized (Table 1, Section [a]). The total enzyme activity in the precipitate was $5.51 \times 10^6$ cpm/h. This represented 306% of the initial total activity of the enzyme. This suggested that the initial total activity had been underestimated, perhaps due to the presence of inhibiting substances in the culture media.

The dialysed and lyophilized crude enzyme gave a much better enzyme activity with a specific activity of 12,000 cpm/mg protein/h (Table 1, Section [b]). On the basis of the above crude enzyme total protein, this would give total enzyme activity of $2.893 \times 10^6$ cpm/h, 16 times its pre-dialysis value. Thus, some of the inhibition suggested above had been removed by dialysis, indicating that at least some of the inhibiting substances were dialysable.

TABLE 1

The distribution of P. haemolytica enzyme activity in acid fractions.

| Enzyme | Specific Activity (cpm/mg protein/h) | Purification (fold) | Total Proteins (mg) | Total Activity (cpm/h × $10^6$) | Recovery of Enzyme (%) |
|---|---|---|---|---|---|
| [a] Crude (before dialysis) | 7,000 ± 140 | 1.0 | 241.5 | 1.8 | 100 |
| Acid ppt. | 126,000 ± 2,800 | 17.0 | 43.6 | 5.5 | 306 ± 8.5 |
| Acid supernatant | 0 | — | 195.2 | — | — |
| [b] Crude enzyme (dialysed and lyophilized) | 12,000 ± 850 | 1.0 | 241.5 | 2.9 ± 0.6 | 100 |
| Acid ppt. (same as in [a] after one week at −5° C.) | 74,000 ± 1,400 | 6.1 | 43.6 | 3.2 | 110. ± 2.8 |

Mean ± S.E.M. (n = 2)

The reconstituted acid precipitate was stored in solution (containing about 7.3 mg protein/ml) in aliquots of 0.5 ml at −5° C. Analysis for enzyme activity after 7 days of storage yielded a specific activity of 74,000 cpm/mg/h. Its purification over the dialysed freeze-dried crude enzyme was 6.1 fold and its total activity was calculated as $3.23 \times 10^6$ cpm/h.

Subsequently, crude enzyme activity was measured only on dialysed and lyophilized crude enzyme, and the purification factor obtained for the acid precipitate consistently varied between 5 and 6.

EXAMPLE 8

Screening of P. haemolytica Serotypes for Radioactive Product-Releasing Enzyme Activity Tritium-labelled ghost cells (25 mg protein/ml) were diluted to obtain a 2.5 mg protein/ml suspension. 14 mg/ml solutions of crude enzyme from each of the 12 recognized P. haemolytica serotypes were prepared by dissolving 14 mg of each crude enzyme 1.0 ml of 0.1 M HEPES buffer pH 7.4. The assay of the crude enzyme for the radioactive product-releasing activity was performed as follows: 50 µl of each of the above crude enzyme preparations (14 mg/ml) were pipetted into duplicate microcentrifuge tubes. Two sets of such preparations were made and 50 µl of penicillin/streptomycin (1600 U/700 µg/ml in HEPES buffer) was added to each. One set of tubes were heated at 100° C. for 15 min to provide the negative control (denatured enzyme) and then cooled to room temperature. Then 0.1 ml of the $^3$H-labelled red cell membrane suspension (0.25 mg protein) was then added to each tube, and after mixing the tubes were incubated at 30° C. for 2 h. After incubation, residual ghost cells were pelleted by centrifuging at 13,000 g for 4 min and 50 µl of the supernatants were counted for radioactivity. Alternatively, 0.1 ml of the supernatant was treated with 0.1 ml of 10% TCA. After 10 min, this was centrifuged at 13,000 g for 4 min and 0.1 ml of the supernatant then counted for radioactivity.

Figure 2:
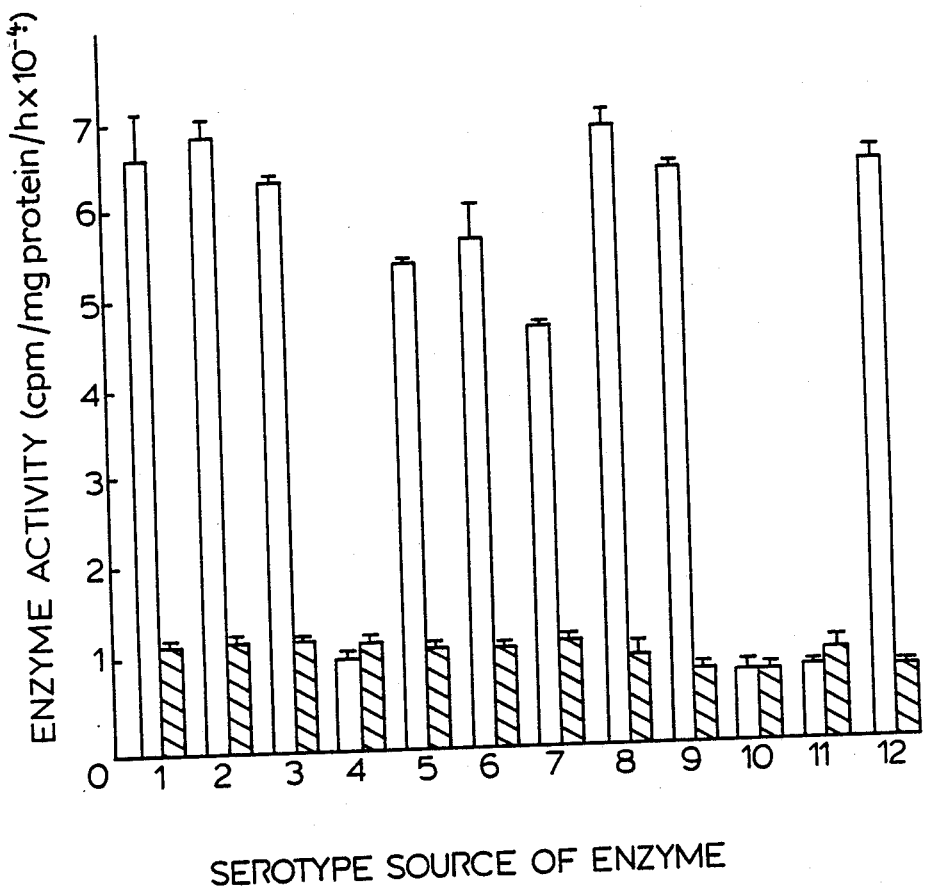
FIG. 2 is a graph setting out enzyme activity of glycoprotease isolated from twelve different serotypes of *P. haemolytica.*

The results for the survey of enzyme production among the 12 recognized serotypes of P. haemolytica (FIG. 2) clearly show that it is not an exclusive property of P. haemolytica serotype 1. Nine out of the 12 serotypes examined were enzyme producers. The only non-producers were serotypes 4, 10 and 11. The specific activities of the enzyme preparations from serotypes 1, 2, 3, 8, 9 and 12 were approximately identical, but were lower for enzyme preparations from serotypes 5, 6, and 7 (FIG. 2). Radioactivity released by enzyme preparations from serotypes 4, 10 and ]1 was the same as background level in each case. Background releases by all enzyme preparations were identical and accounted for less than 15% of total counts released by active enzyme in most cases. The background did not vary with the level of activity of the enzyme.

EXAMPLE 9

The Effect of Protein Concentration in Culture Media on Enzyme Production

To examine the effect of fetal calf serum (FCS) (usually added to the culture medium) on enzyme production, the enzyme was prepared both in the presence and in the absence of fetal calf serum. The general procedure described under the above method was employed with the modifications described here. Bacterial cells (1.0 ml suspension in RPMI, OD 525 =0.45) from brain-heart infusion broth (BHIB) were inoculated into 50 ml of RPMI (1640) in a 100 ml Erlenmeyer flask containing 5% fetal calf serum, and another 100 ml flask containing RPMI (1640) only. Both flasks were incubated at 37° C. for 1.5 h. The culture filtrates were then prepared, dialysed, and lyophilized. The residues were then weighed. A solution of each enzyme preparation was made for enzyme assay as follows: enzyme prepared in 5% fetal calf serum, 10 mg/ml; enzyme prepared without fetal calf serum, 6 mg/ml.

Twenty μl of each of the above enzyme solutions were assayed for enzyme activity. SDS polyacrylamide gel electrophoresis was also performed on the samples using a 9-15% gradient gel.

In another experiment, enzyme preparations were made in 7% and 3% fetal calf serum respectively. In each case, 10 ml of the bacterial cell suspension were inoculated into 500 ml of the medium and the cultures were incubated at 37° C. for 3 h. About 500 ml of culture filtrate were obtained for each preparation and these were dialysed and lyophilized. Solutions, 15 mg/ml, of the preparations were made and 50 μl of each were analyzed for enzyme activity by incubation with 0.2 ml tritiated erythrocyte suspension (0.16 mg protein) in a final volume of 0.3 ml. The specific radioactivity of the ghost cells used was 420,300 cpm/mg protein (0.35 μCi/mg). This was different from that used in the preceding experiment. An aliquot of the test sample was analyzed for radioactivity after incubation.

The results tabulated in Table 2 show that substantial improvement in the activity of the enzyme can be obtained by reducing the amount of fetal calf serum in the culture medium during enzyme preparation. In the absence of fetal calf serum, the yield of enzyme was low but the specific activity was increased almost five-fold when compared with enzyme prepared in 5% fetal calf serum. Total enzyme activity obtained in the absence of fetal calf serum was about 36% of that obtained in the presence of 5% fetal calf serum. This yield was significant in view of the fact that a five-fold increase in enzyme activity was also obtained.

In the second experiment, enzyme was prepared in culture media containing 7% and 3% fetal calf serum respectively. The results (Table 2, Section II) showed that enzyme produced in the medium containing 3% fetal calf serum had a 2.4-fold increase in activity over enzyme prepared in medium containing 7% fetal calf serum. In addition to the improvement in the specific activity of the enzyme, total enzyme production in 3% fetal calf serum was at least marginally superior to production in 7% fetal calf serum.

As demonstrated in the previous experiment (Table 2, Section I), fetal calf serum appears to optimize enzyme production. The above experiment has shown that 3% fetal calf serum sufficiently meets this requirement. It is unnecessary, therefore, to use as much as 7% fetal calf serum in the medium for the purpose of enzyme production.

Enzyme prepared without fetal calf serum did not precipitate at all when adjusted to pH 4.0. Enzyme from culture media which contained 3% fetal calf serum did not form good precipitates either, especially if the culture had been incubated for 3 h at 37° C. However, when 5 to 7% fetal calf serum was present in the culture media, the resulting enzyme preparations formed good precipitates at pH 4.0 and the recovery of enzyme activity was quantitative. This suggests that the enzyme proteins co-precipitate with other proteins in fetal calf serum. In spite of this handicap, acid precipitation was a good first-stage procedure for purifying the enzyme.

TABLE 2

The effect of fetal calf serum concentration on enzyme production and activity.

| | Enzyme Preparation | Yield (mg protein) | Specific Activity (cpm/mg/h) | Total Activity (cpm/h × 10⁶) | % (a) | Relative Activity |
|---|---|---|---|---|---|---|
| I | With 5% FCS | 118.0 | 12,300 ± 280 | 1.5 ± 0.3 | 100.0 ± 2.3 | 1.0 |
| | Without FCS | 9.0 | 58,000 ± 1,400 | 0.5 | 35.9 ± 1.1 | 4.7 |
| II | With 7% FCS | 743.0 | 2,900 ± 560 | 2.1 ± 0.3 | 100 ± 14.3 | 1.0 |
| | With 3% FCS | 427.0 | 6,900 ± 280 | 3.0 ± 0.5 | 137.9 ± 23.8 | 2.4 |

Mean ± S.E.M. (n = 2)
(a) Expressed as a percentage of the specific activity of the enzyme preparation containing the highest concentration of FCS.
I and II were different experiments. Ghost cells used for enzyme assay had different specific activities in each case.

EXAMPLE 10

Determination of the Cleavage of Glycophorin from the Amino Acid Composition of Cleaved Polypeptides The major sialoglycopeptide products obtained from the hydrolysis of erythrocyte membranes with *P. haemolytica* protease had apparent $M_r$ values of 24,000 and about 12,600. These molecular weights were established by electrophoresis analysis of fractions of enzyme products. Fractions from gel filtration and ion exchange chromatographies were examined by SDS polyacroamine gel electrophoresis and staining. The major product of *P. hamolytica* protease digestion of erythrocyte membrane has an apparent $M_r$ of 24 000 This is confirmed in that it was the only product obtained when isolated glycophorin was hydrolysed by the enzyme to determine the site of cleavage of the glycophorin of FIG. 1. An analysis of the C-terminal amino acids on the polypeptides of $M_r$ 24,000 and 12,000 was carried out by hydrazinolysis. These two polypeptides are the major products of the digestion of glycophorins by the enzyme. The analysis revealed that on the C-terminal histidine was present. The amino acid composition of the 24,000 $M_r$ product had suggested that its release could result from cleavage of glycophorin at any point between residues 58 and 73. There are two histidine residues between amino acid residues 58 and 73 and they are found together as shown in FIG. 1 at residues 66 and 67. Cleavage of glycophorin at residues 66 or 67 would produce a product similar to the 24,000 $M_r$ polypeptide cleaved by the *P. haemolytica* glycoprotease. The amino acid composition of the 24,000 $M_r$ product and those of possible glycophorin peptides that would contain C-terminal histidine are compared in the following Table 3. There are some discrepancies in the comparisons, such as for the amino acids Asx, Gly, Val, and Leu. Lys and Arg also show differences. These differences are not unexpected in that the enzyme products are likely derived from all glycophorins, rather than just glycophorin A against which comparisons have been made. The results, however, point to a cleavage at sites 66 and 67 of the glycophorin.

TABLE 3

Comparison of the amino acid composition of the 24,000 $M_r$ enzyme product with those of possible glycophorin peptides containing C-terminal His.

| Amino Acid | P3 (24,000 $M_r$) | Calculated for glycophorin peptides containing C-terminal His. | | | | | |
|---|---|---|---|---|---|---|---|
| | Amino acid in mol/100 mol | | | | | | |
| | | Res. 1-9 | Res. 1-29 | Res. 1-41 | Res. 1-66 | Res. 1-67 | Res. 10-66 |
| Asx | 9.4 ± 0.14 | 0 | 6.7 | 7.3 | 4.5 | 4.5 | 5.3 |
| Thr | 13.9 ± 0.68 | 22.2 | 24.1 | 22.0 | 16.7 | 16.4 | 15.9 |
| Ser | 13.9 ± 0.07 | 16.7 | 25.9 | 20.7 | 15.9 | 15.7 | 15.9 |
| Glx | 12.6 ± 0.71 | 5.6 | 5.2 | 3.7 | 12.9 | 12.7 | 14.0 |
| Pro | 4.2 ± 0.35 | 0 | 0 | 2.4 | 4.5 | 4.5 | 5.3 |
| Gly | 6.8 ± 0.61 | 5.6 | 1.7 | 1.2 | 2.3 | 2.3 | 1.8 |
| Ala | 8.4 ± 0.40 | 11.1 | 3.4 | 9.8 | 7.6 | 7.5 | 7.0 |
| Cys | 0 | 0 | 0 | 0 | 0 | 0 | 0 |
| Val | 5.6 ± 0.42 | 11.1 | 6.9 | 4.9 | 9.0 | 9.0 | 8.8 |
| Met | 0.2 ± 0.05 | 11.1 | 3.4 | 2.4 | 1.5 | 1.5 | 0 |
| Ile | 3.6 ± 0.37 | 0 | 3.4 | 2.4 | 3.0 | 3.0 | 3.5 |
| Leu | 6.6 ± 0.39 | 5.6 | 1.7 | 1.2 | 2.3 | 2.3 | 1.8 |
| Tyr | 3.9 ± 0.92 | 0 | 3.4 | 4.9 | 4.5 | 4.5 | 5.3 |
| Phe | 2.7 ± 0.26 | 0 | 0 | 0 | 0 | 0 | 0 |
| His | 4.7 ± 0.20 | 11.1 | 6.7 | 7.3 | 6.0 | 7.5 | 5.3 |
| Lys | 5.8 ± 0.09 | 0 | 3.4 | 4.9 | 3.0 | 3.0 | 3.5 |
| Arg | 3.6 ± 0.45 | 0 | 0 | 4.9 | 6.1 | 6.0 | 7.0 |

Mean ± SEM (n = 3)

Although preferred embodiments of the invention have been described herein in detail, it will be understood by those skilled in the art that variations may be made thereto without departing from the spirit of the invention or the scope of the appended claims.

The embodiments of the invention in which an exclusive property or privilege is claimed are defined as follows:

1. A glycoproteinase, isolated and purified from culture media of *Pasterurella haemolytica* having the following identifying characteristics whereby said glycoproteinase:
   (i) cleaves glycophorin A on the carboxylate side of histidine at amine acid residue 66 or 67 of said glycophorin as shown in FIG. 1 without general enzyme digestion of other cell protein,
   (ii) is inhibited by metal chelators, and
   (iii) has optimum enzymatic activity at a pH in the range of 7 to 8.5.

2. A method of producing the glycoproteinase of claim 1 specific for cleaving a protein portion having carbohydrate antigen markers from glycoproteins of plant and mammal cell membranes, said process comprising culturing *Pasteurella haemolytica* in a culture medium containing nutrients which induce *Pasteurella haemolytica* to produce said glycoproteinase and release it into said medium, adjusting pH of said medium to 4 to precipitate said glycoproteinase from said medium and recovering said glycoproteinase having said characteristics.

3. A method of claim 2, wherein a source of protein for co-precipitation with said glycoproteinase is added to said medium.

4. A method of claim 3, wherein an acidic buffer is used to adjust pH of said medium to separate said glycoproteinase from said medium.

5. A method of claim 4, wherein said acidic buffer is an acetate buffer.

6. A method of claim 5, wherein said acetate buffer is approximately 0.010 M concentration in said media.

* * * * *